US012723257B2

(12) United States Patent
Ligthart et al.

(10) Patent No.: US 12,723,257 B2
(45) Date of Patent: Sep. 1, 2026

(54) ***Mycosphaerella brassicicola* RESISTANT *Brassica oleracea* PLANTS**

(71) Applicant: Bejo Zaden B.V., Warmenhuizen (NL)

(72) Inventors: Johannes Theodorus Wilhelmus Ligthart, Warmenhuizen (NL); Jan Sybe Wijngaarden, Warmenhuizen (NL); Hubertus Theodorus Maria Janssen, Warmenhuizen (NL); Roelof Marinus Veenstra, Warmenhuizen (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 726 days.

(21) Appl. No.: 17/769,775

(22) PCT Filed: Oct. 17, 2019

(86) PCT No.: PCT/EP2019/078231
§ 371 (c)(1),
(2) Date: Apr. 18, 2022

(87) PCT Pub. No.: WO2021/073744
PCT Pub. Date: Apr. 22, 2021

(65) Prior Publication Data
US 2022/0372507 A1 Nov. 24, 2022

(51) Int. Cl.
*C12N 15/82* (2006.01)
*C12Q 1/68* (2018.01)
*C12Q 1/6895* (2018.01)

(52) U.S. Cl.
CPC ....... *C12N 15/8282* (2013.01); *C12Q 1/6895* (2013.01); *C12Q 2600/13* (2013.01); *C12Q 2600/156* (2013.01)

(58) Field of Classification Search
CPC .............. C12N 15/8282; C12Q 1/6895; C12Q 2600/156
See application file for complete search history.

(56) References Cited

U.S. PATENT DOCUMENTS 8,492,615 B2 7/2013 Barten

FOREIGN PATENT DOCUMENTS

WO 2007116096 A1 10/2007

OTHER PUBLICATIONS

Abuyusuf et al. 2018, Altered glucosinolate profiles and expression of glucosinolate biosynthesis genes in ringspot-resistant and susceptible cabbage lines. International Journal of Molecular Sciences, 19(9), 2833 (cited reference in Information disclosure statement (IDS) filed on Jul. 15, 2022). (Year: 2018).*

Bezo et al. (WIPO International Publication No. WO 2007/116096 A1, Publication Date: Oct. 18, 2007) (cited reference IDS filed on Jul. 15, 2022). (Year: 2007).*

Van Den Ende et al., 1992, A screening test for Mycosphaerella brassicicola on *Brassica oleracea*. Netherlands Journal of Plant Pathology, 98, 227-236 (cited reference in IDS filed on Jul. 15, 2022). (Year: 1992).*

Mauricio, 2001, Mapping Quantitative Trait Loci in Plants: Uses and Caveats for Evolutionary Biology, Nature Reviews Genetics 2:370-381. (Year: 2001).*

Definition of Genome, National Cancer Institute, Accessed at https://www.genome.gov/genetics-glossary/Genome, in Feb. 10, 2025. (Year: 2025).*

Handbook of Intellectual property information and Documentation standards-ST.26, p. 3.26.i.2, accessed at https://www.wipo.int/export/sites/www/standards/en/pdf/03-26-01_v1_6.pdf, on Feb. 14, 2025. (Year: 2025).*

Abuyusuf et al., "Altered Glucosinolate Profiles and Expression of Glucosinolate Biosynthesis Genes in Ringspot-Resistant and Susceptible Cabbage Lines", Int. J. Mol. Sci., 2018, pp. 1-19, vol. 19.

Database EMBL, "*Brassica oleracea* var. viridis mRNA, clone: KALE-115K16, 5' end sequence," database accession No. DK499781.

Database EMBL, "BONRO53TR BO_1.6_2_KB_tot *Brassica oleracea* genomic clone BONRO53, genomic survey sequence," database accession No. BZ502434.

Van Den Ende, "A screening test for Mycosphaerella brassicicola on *Brassica oleracea*", Neth. J. Pl. Path., 1992, pp. 227-236, vol. 98.

* cited by examiner

*Primary Examiner* — David H Kruse
*Assistant Examiner* — Santosh Sharma
(74) *Attorney, Agent, or Firm* — The Webb Law Firm

(57) ABSTRACT

Provided herein are *Mycosphaerella brassicicola* resistant *Brassica oleracea* plants including a resistance providing genomic fragment including SEQ ID Nos. 1 and 3. The present *Mycosphaerella brassicicola* resistant *Brassica oleracea* plants do not include a resistance providing genomic fragment comprising SEQ ID Nos. 2 and 4. Also provided herein are methods for identifying the present plants and the use of the disclosed sequences for identifying *Mycosphaerella brassicicola* resistant *Brassica oleracea* plants.

7 Claims, No Drawings

Specification includes a Sequence Listing.

SEQUENCE LISTING

```
<160> NUMBER OF SEQ ID NOS: 26

<210> SEQ ID NO 1
<211> LENGTH: 401
<212> TYPE: DNA
<213> ORGANISM: Brassica oleracea

<400> SEQUENCE: 1

ctggaatgac cagtgaggaa cctcacacta gttgcaacac ctcgatgcgt taagggaatc    60

ccaagctctg ctgctatccc cgacgcagca gtaatcccag ggataacttg aactcggatc   120

ccttgctgtt gcagaaagtc catttcttcc ccrcctcgtc caaaaaccag aggatctcca   180

cctttaagcc tcacaacagt cgcaccagct tcagcaaaac ttaggagcag ttcatgtatc   240

tcctcctgag ttctgctatg ataaccagca gttttgccga catagagaag cctagcatca   300

ggagcaacca actccagaac atcattagag acaagcctgt cgtaaagcaa aagatcagcg   360

ctttgaatga ctctgacagc tttcaaagtc aaaagctctg g                       401


<210> SEQ ID NO 2
<211> LENGTH: 401
<212> TYPE: DNA
<213> ORGANISM: Brassica oleracea

<400> SEQUENCE: 2

ctggaatgac cagtgaggaa cctcacacta gttgcaacac ctcgatgcgt taagggaatc    60

ccaagctctg ctgctatccc cgacgcagca gtaatcccag ggataacttg aactcggatc   120

ccttgctgtt gcagaaagtc catttcttcc ccrcctcgtc caaaaaccag aggatctcca   180

cctttaagcc tcacaacagt agcaccagct tcagcaaaac ttaggagcag ttcatgtatc   240

tcctcctgag ttctgctatg ataaccagca gttttgccga catagagaag cctagcatca   300

ggagcaacca actccagaac atcattagag acaagcctgt cgtaaagcaa aagatcagcg   360

ctttgaatga ctctgacagc tttcaaagtc aaaagctctg g                       401
```

<210> SEQ ID NO 3
<211> LENGTH: 248
<212> TYPE: DNA
<213> ORGANISM: Brassica oleracea

<400> SEQUENCE: 3

```
aacttcttta gcgatttgcc tccagtgacc atataaacga tgcaaacgcc tatttccacg     60

atcagctgtt gcggcacgac tatgtaaaga ccgagttttt ccccgaacgc gtgttgtccg    120

agctcgtggt agcgatcgaa acgctttccc ggaaccattt cgtgcatttc taccatttgc    180

cataatgtgt atagtgttat gatccatgag agaaccatta ctgtaattcc tggtccccag    240

ccgagctg                                                             248
```

<210> SEQ ID NO 4
<211> LENGTH: 248
<212> TYPE: DNA
<213> ORGANISM: Brassica oleracea

<400> SEQUENCE: 4

```
aacttcttta gcgatttgcc tccagtgacc atataaacga tgcaaacgcc tatttccacg     60

atcagctgtt gcggcacgac tatgtaaaga ccgagttttt ccccgaacgc gtgttgtccg    120

agctcgtggt agcgatcgaa acgctttccc ggaaccattt cgtgcatttc taccatttgc    180

cataatgtgt atagtgttat catccatgag agaaccatta ctgtaattcc tggtccccag    240

ccgagctg                                                             248
```

<210> SEQ ID NO 5
<211> LENGTH: 317
<212> TYPE: DNA
<213> ORGANISM: Brassica oleracea

<400> SEQUENCE: 5

```
attgtgtata tagatgatca atccagctaa aaataagaat gaaagggaat atgcatatag     60

acaaggggc acatcggagt ctgatgagag agatgcatga ggaggtttgg tttttataat    120

taacagagat gctgtgatgc aagacaagaa taagtacact ttgtcgagta cagatgtggt    180

gaggaagaga agcgtgcaga tgcaaagtcg gaagtcatat tcatctactc gtcgtccgat    240

ggcagctgga gatgatggaa ctcgatttgg aaggaggact cttgtggttt ggacttgtgc    300

cgccttaaat acctcac                                                   317
```

<210> SEQ ID NO 6
<211> LENGTH: 317
<212> TYPE: DNA
<213> ORGANISM: Brassica oleracea

<400> SEQUENCE: 6

```
attgtgtata tagatgatca atccagctaa aaataagaat gaaagggaat atgcatatag     60

acaaggggc acatcggagt ctgatgagag agatgcatga ggaggtttgg tttttacaat    120

taacagagat gctgtgatgc aagacaagaa taagtacact ttgtcgagta cagatgtggt    180

gaggaagaga agcgtgcaga tgcaaagtcg gaagtcatat tcatctactc gtcgtccgat    240

ggcagctgga gatgatggaa ctcgatttgg aaggaggact cttgtggttt ggacttgtgc    300

cgccttaaat acctcac                                                   317
```

<210> SEQ ID NO 7
<211> LENGTH: 401
<212> TYPE: DNA

<213> ORGANISM: Brassica oleracea

<400> SEQUENCE: 7

```
gtctgatgag agagatgcat gaggaggttt ggtttttata attaacagag atgctgtgat     60
gcaagacaag aataagtaca ctttgtcgag tacagatgtg gtgaggaaga gaagcgtgca    120
gatgcaaagt cggaagtcat attcatctac tcgtcgtccg atggcagctg gagatgatgg    180
aactcgattt ggaaggagga ctcttgtggt ttggacttgt gccgccttaa atacctcacg    240
agtctccctc tggtccttgg gaacatgttc tcgtcgtcgt cggcgatatt catctcctcc    300
gccttggaat cctctaactt cacggcgtta gtgttgatga actcctcctc ttctttagac    360
ttcaaagtcg aaatcatatt ctccatgagg cgtttcactt c                        401
```

<210> SEQ ID NO 8
<211> LENGTH: 401
<212> TYPE: DNA
<213> ORGANISM: Brassica oleracea

<400> SEQUENCE: 8

```
gtctgatgag agagatgcat gaggaggttt ggtttttata attaacagag atgctgtgat     60
gcaagacaag aataagtaca ctttgtcgag tacagatgtg gtgaggaaga gaagcgtgca    120
gatgcaaagt cggaagtcat attcatctac tcgtcgtccg atggcagctg gagatgatgg    180
aactcgattt ggaaggagga gtcttgtggt ttggacttgt gccgccttaa atacctcacg    240
agtctccctc tggtccttgg gaacatgttc tcgtcgtcgt cggcgatatt catctcctcc    300
gccttggaat cctctaactt cacggcgtta gtgttgatga actcctcctc ttctttagac    360
ttcaaagtcg aaatcatatt ctccatgagg cgtttcactt c                        401
```

<210> SEQ ID NO 9
<211> LENGTH: 401
<212> TYPE: DNA
<213> ORGANISM: Brassica oleracea

<400> SEQUENCE: 9

```
cggaactctt ggttcagaca ctggtctatt tcagatgtca ctatcttcaa tgccggaaac     60
cgtttgcaga cacaatgaat tccttctggc gccgagataa ggttgaggaa gatgatgtga    120
gattcaggaa ctcctttctg tatgagtagt tcaatggctt gattagcaga gttacctgta    180
gctaagacag gatctagaag taggacatga cgttcagaga tgtcttgagg aagcttctca    240
tatataagct gttttccatt gtctccaaca cggtggataa gaatcttccc taacttaatc    300
cctttgcagc aagcgcgtaa tgcgttttcc atgctttcac cacttcgaat aatagagatc    360
ccacaaagtt tcttgcagaa atcaactcca gtgtacacag c                        401
```

<210> SEQ ID NO 10
<211> LENGTH: 401
<212> TYPE: DNA
<213> ORGANISM: Brassica oleracea

<400> SEQUENCE: 10

```
cggaactctt ggttcagaca ctggtctatt tcagatgtca ctatcttcaa tgccggaaac     60
cgtttgcaga cacaatgaat tccttctggc gccgagataa ggttgaggaa gatgatgtga    120
gattcaggaa ctcctttctg tatgagtagt tcaatggctt gattagcaga gttacctgta    180
gctaagacag gatctagaag caggacatga cgttcagaga tgtcttgagg aagcttctca    240
tatataagct gttttccatt gtctccaaca cggtggataa gaatcttccc taacttaatc    300
```

cctttgcagc aagcgcgtaa tgcgttttcc atgctttcac cacttcgaat aatagagatc 360
ccacaaagtt tcttgcagaa atcaactcca gtgtacacag c 401

<210> SEQ ID NO 11
<211> LENGTH: 202
<212> TYPE: DNA
<213> ORGANISM: Brassica oleracea

<400> SEQUENCE: 11
catctactcg agaaagtgtt tcatcacttg cttgtgagtt ggtttcgaaa ctgtctccwa 60
gagaatgctg atcatgcatg tttgcgwacg acccatcact aagttctttg tcrtctgcaa 120
gtggchgagh wgaatcatct gaatgggcag agagyaattc tgcacgagga acttgagaac 180
tctgrtccat cgctgcdaag ta 202

<210> SEQ ID NO 12
<211> LENGTH: 201
<212> TYPE: DNA
<213> ORGANISM: Brassica oleracea

<400> SEQUENCE: 12
catctactcg agaaagtgtt tcatcacttg cttgtgagtt ggtttcgaaa ctgtctccwa 60
gagaatgctg atcatgcatg tttgcgwacg acccatcact tagttctttg tcrtctgcaa 120
gtggchgagh wgaatcatct gaatgggcag agagyaattc tgcacgagga acttgagaac 180
tctgrtccat cgctgcaagt a 201

<210> SEQ ID NO 13
<211> LENGTH: 201
<212> TYPE: DNA
<213> ORGANISM: Brassica oleracea

<400> SEQUENCE: 13
agggcttctt catcctaaag ctccattaaa gcagcwtcgg tttstgacaa aggagctaac 60
aagtcttcgt aggtatctga taacagggac gagtccatta ttaatggtgg agagaacact 120
tggtcttcaa cgtcgtaaaa cgattgthgt gcatcagaag ctacactgtt cgatccagct 180
actgagagaa acscgttccc g 201

<210> SEQ ID NO 14
<211> LENGTH: 201
<212> TYPE: DNA
<213> ORGANISM: Brassica oleracea

<400> SEQUENCE: 14
agggcttctt catcctaaag ctccattaaa gcagcwtcgg tttstgacaa aggagctaac 60
aagtcttcgt aggtatctga taacagggac gagtccatta gtaatggtgg agagaacact 120
tggtcttcaa cgtcgtaaaa cgattgthgt gcatcagaag ctacactgtt cgatccagct 180
actgagagaa acscgttccc g 201

<210> SEQ ID NO 15
<211> LENGTH: 201
<212> TYPE: DNA
<213> ORGANISM: Brassica oleracea
<220> FEATURE:
<221> NAME/KEY: misc_feature
<222> LOCATION: (123)..(123)
<223> OTHER INFORMATION: n is a, c, g, or t

<400> SEQUENCE: 15
agagagagtt ccattttcat caggtcaaac ccaccggaga ctcgggagga tcaatggcgg 60
cgatactaat cggaagagcc ttcaaatcag ctagagtcgt ccgtgctcga tctttctgca 120
cancgtctgc tgctcgtmaa cccgactccg atggccastc atcggaacct tcttcctcgt 180
cttcgttcac kttcgacaag g 201

<210> SEQ ID NO 16
<211> LENGTH: 201
<212> TYPE: DNA
<213> ORGANISM: Brassica oleracea
<220> FEATURE:
<221> NAME/KEY: misc_feature
<222> LOCATION: (123)..(123)
<223> OTHER INFORMATION: n is a, c, g, or t

<400> SEQUENCE: 16
agagagagtt ccattttcat caggtcaaac ccaccggaga ctcgggagga tcaatggcgg 60
cgatactaat cggaagagcc ttcaaatcag ctagagtcgt tcgtgctcga tctttctgca 120
cancgtctgc tgctcgtmaa cccgactccg atggccastc atcggaacct tcttcctcgt 180
cttcgttcac kttcgacaag g 201

<210> SEQ ID NO 17
<211> LENGTH: 201
<212> TYPE: DNA
<213> ORGANISM: Brassica oleracea
<220> FEATURE:
<221> NAME/KEY: misc_feature
<222> LOCATION: (33)..(33)
<223> OTHER INFORMATION: n is a, c, g, or t

<400> SEQUENCE: 17
ctagagtcgt ycgtgctcga tctttctgca cancgtctgc tgctcgtmaa cccgactccg 60
atggccastc atcggaacct tcttcctcgt cttcgttcac tttcgacaag gaaagcgaga 120
aacccatcct cgtgaaagcc ccgaacgctc grcggaacaa cgaytcggat tcggtgacga 180
tgccgacgtc tttcatgacg g 201

<210> SEQ ID NO 18
<211> LENGTH: 201
<212> TYPE: DNA
<213> ORGANISM: Brassica oleracea
<220> FEATURE:
<221> NAME/KEY: misc_feature
<222> LOCATION: (33)..(33)
<223> OTHER INFORMATION: n is a, c, g, or t

<400> SEQUENCE: 18
ctagagtcgt ycgtgctcga tctttctgca cancgtctgc tgctcgtmaa cccgactccg 60
atggccastc atcggaacct tcttcctcgt cttcgttcac gttcgacaag gaaagcgaga 120
aacccatcct cgtgaaagcc ccgaacgctc grcggaacaa cgaytcggat tcggtgacga 180
tgccgacgtc tttcatgacg g 201

<210> SEQ ID NO 19
<211> LENGTH: 201
<212> TYPE: DNA
<213> ORGANISM: Brassica oleracea

<400> SEQUENCE: 19
aagatatgca tgattgggca gcaccgttga tagcttcggc tctattcgcg tttctatcgc 60
cggggctgat actgcagttt cctgggaaag aatctccggt tggtttcatg aacatgaara 120
cgacgatagc ttctattttc gtccacaccg ttctctacgg tctstttctc atcctcttcc 180
tagtcgttct caacgtccat g 201

<210> SEQ ID NO 20
<211> LENGTH: 201
<212> TYPE: DNA
<213> ORGANISM: Brassica oleracea

<400> SEQUENCE: 20
aagatatgca tgattgggca gcaccgttga tagcttcggc tctattcgcg tttctatcgc 60
cggggctgat actgcagttt cctgggaaag aatctccggt aggtttcatg aacatgaara 120
cgacgatagc ttctattttc gtccacaccg ttctctacgg tctstttctc atcctcttcc 180
tagtcgttct caacgtccat g 201

<210> SEQ ID NO 21
<211> LENGTH: 201
<212> TYPE: DNA
<213> ORGANISM: Brassica oleracea

<400> SEQUENCE: 21
cagcaccgtt gatagcttcg gctctattcg cgtttctatc gccggggctg atactgcagt 60
ttcctgggaa agaatctccg gtwggtttca tgaacatgaa aacgacgata gcttctattt 120
tcgtccacac cgttctctac ggtctstttc tcatcctctt cctagtcgtt ctcaacgtcc 180
atgtttatgc ttagctttag c 201

<210> SEQ ID NO 22
<211> LENGTH: 201
<212> TYPE: DNA
<213> ORGANISM: Brassica oleracea

<400> SEQUENCE: 22
cagcaccgtt gatagcttcg gctctattcg cgtttctatc gccggggctg atactgcagt 60
ttcctgggaa agaatctccg gtwggtttca tgaacatgaa gacgacgata gcttctattt 120
tcgtccacac cgttctctac ggtctstttc tcatcctctt cctagtcgtt ctcaacgtcc 180
atgtttatgc ttagctttag c 201

<210> SEQ ID NO 23
<211> LENGTH: 146
<212> TYPE: DNA
<213> ORGANISM: Brassica oleracea

<400> SEQUENCE: 23
taagtctctt ttgctcaart acctttttca gttattccaa aaataaagct tctatctgag 60
cttatctgtt tgtagaattg atgattgtaa gggttacatc gatacaggaa tgaaaytaaa 120
gccagagttt cttgcaaaaa aaaaaa 146

<210> SEQ ID NO 24
<211> LENGTH: 146
<212> TYPE: DNA
<213> ORGANISM: Brassica oleracea

<400> SEQUENCE: 24
taagtctctt ttgctcaart acctttttca gttattccaa aaataaagct tctatctgag 60

-continued

```
cttatctgtt tgtagaattg atgattgtaa gggttacatc aatacaggaa tgaaaytaaa    120

gccagagttt cttgcaaaaa aaaaaa                                         146


<210> SEQ ID NO 25
<211> LENGTH: 201
<212> TYPE: DNA
<213> ORGANISM: Brassica oleracea

<400> SEQUENCE: 25

aatgatacaa cattgaagaa acatactctt agwttgatct tccatcagat aaacccagca     60

ggaagtgact gaaacatact cttgggcgat cttkcattat ttaaaaaccc atcatcgacg    120

tttatataaa catgctttca actccggcca ctcgattttc ttcttatttg aattaaactg    180

ctccttttc ttgaaatgca a                                               201


<210> SEQ ID NO 26
<211> LENGTH: 201
<212> TYPE: DNA
<213> ORGANISM: Brassica oleracea

<400> SEQUENCE: 26

aatgatacaa cattgaagaa acatactctt agwttgatct tccatcagat aaacccagca     60

ggaagtgact gaaacatact cttgggcgat cttkcattat ataaaaaccc atcatcgacg    120

tttatataaa catgctttca actccggcca ctcgattttc ttcttatttg aattaaactg    180

ctccttttc ttgaaatgca a                                               201
```

*Mycosphaerella brassicicola* RESISTANT *Brassica oleracea* PLANTS

CROSS-REFERENCE TO RELATED APPLICATION

This application is the United States national phase of International Application No. PCT/EP2019/078231 filed Oct. 17, 2019, the disclosure of which is hereby incorporated by reference in its entirety.

The Sequence Listing associated with this application is filed in electronic format via EFS-Web and is hereby incorporated by reference into the specification in its entirety. The name of the text file containing the Sequence Listing is 2202090 ST25.txt. The size of the text file is 12,366 bytes, and the text file was created on Mar. 31, 2022.

DESCRIPTION

The present invention relates to *Mycosphaerella brassicicola* resistant *Brassica oleracea* plants comprising a resistance providing genomic fragment comprised of SEQ ID Nos. 1 and 3. The present *Mycosphaerella brassicicola* resistant *Brassica oleracea* plants do not comprise a resistance providing genomic fragment comprising SEQ ID Nos. 2, 4, 6, 8, 10, 12, 14, 16, 18, 20, 22, 24, and 26. The present invention further relates to methods for identifying the present plants and the use of the disclosed sequences for identifying *Mycosphaerella brassicicola* resistant *Brassica oleracea* plants.

Cabbage, or *Brassica oleracea*, is grown globally as a food crop; typically almost every part of the plant can be used for consumption. Several cultivars of *B. oleracea* exist, including headed cabbage, savoy cabbage, borecole and point headed cabbage (edible part: leaves); broccoli, sprouting broccoli, Romanesco and cauliflower (edible are the flower heads); Brussels sprouts (used for the lateral buds) and kohlrabi (edible part: the hypocotyl here as thickened part of the stem of the plant). All these vegetables have in common that they are rich in essential nutrients, including vitamin C. A diet rich in cruciferous vegetables is also connected to a reduced risk of some types of human cancers.

As is the case in many cultivated crops, *B. oleracea* is challenged by several diseases and pests. Among these is *Mycosphaerella brassicicola*, belonging to the Ascomycota, a widespread fungal disease which affects a.o. cabbage plants. The disease is common known as ring spot disease. Historically, *M. brassicicola* is most noted on brussels sprouts, winter cauliflower and cabbage.

The pathogen can reproduce both sexually and asexually. Conidia produced from asexual reproduction may cause spots upon host leaves, however such marks are not known to induce disease from infection.

Ascospores, produced by the pathogen through its sexual reproductive stage, infect host plants by entering the plant by germination and simultaneously penetrating the stomata. Ascospores are bicellular and eight of these are contained within each ascus inside of their corresponding perithecium. The fruiting bodies require moisture to facilitate their reproduction and tend to form after a period of very high relative humidity lasting at least four days; preferably at a temperature from 20-26° C. The longer the duration of the wet period, the more severe the infection may spread, with ascospores traveling between crops transported by wind.

Infection is most noted on the leaves of the host, but spores are technically able to cause disease on any above ground part of the plant. Lesions tend to appear around 10 to 14 days following fungal infection. Small black spots of conidia within pycnidia, and ascospores within perithecia, can be seen forming upon concentric ring-shaped lesions. Both spore types develop lesions, though the sexual ascospores tend to create larger more spherical rings.

The ring shaped lesions produced by ascospore infection will terminate at the veins of leaves, which may restrict the characteristic circular nature of the signs of *M. brassicicola*. The ring symptoms may initially be green-brown or grey-black in color; then they will progress until grey when dry and turning black when wet. The outer edge typically forms a ring of chlorosis around the necrotic tissue within the lesion. The rings originate as 3 to 5 mm diameter spots that can potentially grow up to 2 to 3 cm. If the infection spreads far enough it may lead to premature defoliation of the host. Lesions caused by *M. brassicicola* can in turn be the entry gate for a range of other, secondary diseases as *Botrytis* sp.

The fungus will survive on plant parts left in the soil; next to *Brassica* species this is *Raphanus sativus* as an important host; also cruciferous weeds as *Hirschfeldia incana, Matthiola incana, Sisymbrium officinale* and *Thlaspi arvense* can be hosts to the pathogen.

All these circumstances make it difficult to control the disease, especially in areas of intensive vegetable production, because of large numbers of available airborne spores where environmental conditions are cool and wet, thus favoring spread and infection.

One possibility is the application of fungicides, as Benomyl, chlorothalonil, difenoconazole or thiophanate-methyl. The application of fungicides is, however more and more restricted due to environmental and health reasons. Further, combatting the pathogen chemically is difficult since the ideal timing of application of fungicides is hard to determine.

The damage inflicted on the infected plants will result in substantial losses in harvestable crop, where also marketability is lost. This resulting damage is an economical problem which needs a durable and sustainable solution.

Taking into account the problems outlined above, it is a goal for (vegetable) plant breeding to develop resistant plants harboring one or more resistance genes or genetic loci contributing to resistance to this pathogen. This approach also contributes to a more sustainable production of the crop involved.

In general, resistance can be monogenic, i.e. determined by one locus or gene, or can be depending on more loci or genes. In the latter case, these genes can be additive, resulting in Quantitative Trait Loci or QTL's.

The availability of marker sequences linked to the resistance gene or genes contributes to the acceleration of the process of breeding whereas *B. oleracea* is a biannual crop.

As soon as the use of specific DNA markers, linked to a resistance gene is established, these markers can be applied by identifying resistant plants in the offspring from crosses. This can result in a rapid development of several related *B. oleracea* crops where the resistance gene is, or resistance genes are, introduced from one common parental line harboring the resistance trait. With the application of these specific DNA markers, the life cycle of *B. oleracea*, which is generally biannual, can be forced in an annual life cycle where the offspring is directly tested for the presence of the trait rather than subjected to time consuming field tests. Due to the application of molecular markers, the researcher is no longer limited by the biannual life cycle of *B. oleracea* for testing the resistance to the pathogen. The young offspring can directly be tested for the presence of the resistance defining locus and thus the result is not dependent of the plant seedling maturity.

Breeding for resistance generally is performed by making a first cross between susceptible genetic material which has a high level of agronomical quality, and a source of resistance. Selected resistant offspring is repeatedly backcrossed to the same parental quality line under selection for both quality and resistance to the pathogen involved, here *M. brassicicola*. Further, the breeding steps can be accelerated by application of cell biological techniques as doubled haploid induction (anther culture or microspore culture) where in one generation an ultimate level of genetic purity is attained.

SUMMARY

Considering the above, it is an object of the present invention, amongst others, to provide novel *Mycosphaerella brassicicola* resistant providing genomic fragments and plants comprising these fragments.

The present invention meets the above object, amongst other objects, as outlined in the appended claims.

Specifically, the present invention meets the above object, amongst other objects by providing *Mycosphaerella brassicicola* resistant *Brassica oleracea* plants comprising a resistance providing genomic fragment comprising SEQ ID Nos. 1 and 3.

SEQ ID Nos. 1 and 3 are comprised in a genomic fragment on chromosome 4 between base pair positions spanning approximately 50,000e pairs. Considering an average gene length in plants of 240,000 to 250,000 base pairs, it is assumed that the present resistance is encoded by a single gene. Further, the gene located on the present resistance providing genomic fragment is dominant. Considering, the relative small size of the present resistance providing genomic fragment, a skilled person can readily, for example by sequencing and analysis, isolate the presently provided *Mycosphaerella brassicicola* resistance.

According to a preferred embodiment, the present *Mycosphaerella brassicicola* resistant *Brassica oleracea* plants do not comprise a resistance providing genomic fragment comprising SEQ ID Nos. 2 and 4. Although SEQ ID Nos. 2 and 4 share more than 99% sequence identity with SEQ ID Nos. 1 and 3, respectively, no *Mycosphaerella brassicicola* resistance is observed in *Brassica oleracea* plants comprising a genomic fragment comprising SEQ ID Nos. 2 and 4.

The present resistance providing genomic fragment is preferably further characterized by comprising one or more sequences selected from the group consisting of SEQ ID No. 5, SEQ ID No. 7, SEQ ID No. 9, SEQ ID No. 11, SEQ ID No. 13, SEQ ID No. 15, and SEQ ID No. 17 and SEQ ID No. 23. Preferably, the present resistance providing genomic fragment comprises all these sequences. Accordingly, the present invention relates to resistance providing genomic fragments comprised of SEQ ID No. 1, SEQ ID No. 3, SEQ ID No. 5, SEQ ID No. 7, SEQ ID No. 9, SEQ ID No. 11, SEQ ID No. 13, SEQ ID No. 15, and SEQ ID No. 17 and SEQ ID No. 23.

The present resistance providing genomic fragment is preferably further characterized by not comprising one or more sequences selected from the group consisting of SEQ ID No. 6, SEQ ID No. 8, SEQ ID No. 10, SEQ ID No. 12, SEQ ID No. 14, SEQ ID No. 16, and SEQ ID No. 18 and SEQ ID No. 24. Preferably, the present resistance providing genomic fragment does not comprise all these sequences.

Accordingly, the present invention relates to resistance providing genomic fragments not comprised of SEQ ID No. 2, SEQ ID No. 4, SEQ ID No. 6, SEQ ID No. 8, SEQ ID No. 10, SEQ ID No. 12, SEQ ID No. 14, SEQ ID No. 16, and SEQ ID No. 18 and SEQ ID No. 24.

On the left side of the present genomic fragment SEQ ID No. 19, SEQ ID No. 21 were identified and, accordingly these sequences allow identification, amplification, isolation and characterization of the present genomic fragment.

On the right side of the present genomic fragment SEQ ID No. 25 was identified. Accordingly this sequence allows identification, amplification, isolation and characterization of the present genomic fragment, possibly in combination with the above left side sequences.

With respect to the left and right side genomic sequences characterizing the present resistance providing genomic fragment, it is noted that the present resistance is not characterized by the corresponding genomic sequences of SEQ ID No. 20 and/or SEQ ID No. 22 (left) and SEQ ID No. 26 (right).

According to an especially preferred embodiment of the present invention, the present resistance providing genomic fragment is obtainable, obtained or derived from a *Brassica* plant of which representative seeds are deposited under NCIMB 43445 of Jul. 25, 2019 at the NCIMB (NCIMB Limited, Ferguson Building; Craibstone Estate, Bucksburn ABERDEEN, Scotland, AB21 9YA United Kingdom).

Within the context of the present invention the following *Brassica oleracea* plant are contemplated. *B. oleracea* convar. *botrytis* var. *botrytis* (cauliflower, Romanesco), *B. oleracea* convar. *botrytis* var. *cymosa* (broccoli), *B. oleracea* convar. *botrytis* var. *asparagoides* (sprouting broccoli), *B. oleracea* convar. *oleracea* var. *gemnifera* (Brussels sprouts), *B. oleracea* convar. *capitata* var. *alba* (white cabbage, point headed cabbage), *B. oleracea* convar. *capitata* var. *rubra* (red cabbage), *B. oleracea* convar. *capitata* var. *sabauda* (savoy cabbage), *B. oleracea* convar. *acephala* var. *sabellica* (borecole), *B. oleracea* convar. *acephela* var. *gongylodes* (kohlrabi) en *B. oleracea* var. *tronchuda* syn. *costata* (Portuguese cabbage).

According to an especially preferred embodiment the present plants are genetically not stable hybrid plants. In the present context, genetically unstable indicated that the present segregating hybrid plant can not be propagated unchanged.

The present invention also relates to a method for identifying a *Mycosphaerella brassicicola* resistant *Brassica oleracea* plant as defined above comprising the step of establishing the presence a resistance providing genomic fragment comprising one or more nucleic acid sequences selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23 and SEQ ID No. 25 in the genome of the *Mycosphaerella brassicicola* resistant *Brassica oleracea* plant.

The present invention further relates to the use of one or more of nucleic acid sequences selected from the group consisting SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23 and SEQ ID No. 25 for identifying a *Mycosphaerella brassicicola* resistant *Brassica oleracea* plant.

Further, the present invention relates to methods for providing a *Mycosphaerella brassicicola* resistant *Brassica oleracea* plants comprising the step of introgressing a resistance providing genomic fragment as defined above into a *Brassica oleracea* plant, preferably a *Mycosphaerella brassicicola* susceptible *Brassica oleracea* plant.

Furthermore, the present invention relates to nucleic acid sequence selected from the group consisting of SEQ ID No. 1 to SEQ ID No. 26.

DETAILED DESCRIPTION

The present invention will be further detailed in the following example.

Example

Determining Resistance to *M. brassicicola*

Disease tests were performed in a field where *M. brassicicola* infection occurs by the ascospores present. No artificial infection is performed described. After 10 to 14 days the symptoms of *M. brassicicola* infection are assessed and scored on a scale from 0 (plant is dead) to 9 (plant has no symptoms).

Molecular Characterization of Genomic DNA and Mapping of the Resistance Gene

Several backcross populations were produced by crossing and repeated backcrossing of the source of resistance, deposited as NCIMB 43445 and a variety of *B. oleracea* cultivars.

A set of SNP markers were developed by comparing sequence data from lines susceptible and resistant to *M. brassicicola*. These SNP markers were repeatedly mapped on different *Brassica* populations and by selecting cross-overs. With these cross-over generations, the mapped region was narrowed down. The reference genome was the broccoli (*B. oleracea* convar. *botrytis* var. *cymosa*) HDEM assembly as described.

The analysis of several generations of plants made it possible to reduce the genetic location of the resistance gene to an area of ~50,000 bp which corresponds to approx. 0.3% of this chromosome. Sequences analysis of the area identified yielded the present uneven SEQ ID Nos. 1 to 25. Similarly, sequence analysis of the corresponding area in susceptible plants yielded the present even SEQ ID Nos. 2 to 26. Accordingly, a large number of genomic sequences could be identified enabling a precise and rapid identification of plants harboring the gene resulting in resistance to *M. brassicicola*. Individual plants were selected by breeders from the several backcross programmes where the disease resistance was combined with the highest level of agronomical quality.

The invention claimed is:

1. A *Mycosphaerella brassicicola* resistant *Brassica oleracea* plant, representative seed having been deposited under NCIMB 43445, the plant comprising a resistance providing genomic fragment comprising SEQ ID No. 1, SEQ ID No. 3, SEQ ID No. 5, and SEQ ID No. 7.

2. The *Mycosphaerella brassicicola* resistant *Brassica oleracea* plant according to claim 1, wherein the resistance providing genomic fragment is flanked on the left side by SEQ ID No. 19 and/or SEQ ID No. 21 and on the right side by SEQ ID No. 25.

3. The *Mycosphaerella brassicicola* resistant *Brassica oleracea* plant according to claim 1, wherein the plant is a hybrid plant.

4. A method for providing a *Mycosphaerella brassicicola* resistant *Brassica oleracea* plant, wherein the method comprises;

crossing the *Mycosphaerella brassicicola* resistant *Brassica oleracea* plant according to claim 1 with a *Brassica oleracea* plant that is susceptible to *Mycosphaerella brassicicola*, and selecting progeny that are resistant to *Mycosphaerella brassicicola.*

5. A seed or plant part of the *Mycosphaerella brassicicola* resistant *Brassica oleracea* plant according to claim 1.

6. A *Mycosphaerella brassicicola* resistant *Brassica oleracea* plant produced by the method according to claim 4 and comprising in its genome the resistance providing genomic fragment comprising SEQ ID No. 1, SEQ ID No. 3, SEQ ID No. 5, and SEQ ID No. 7.

7. A seed or plant part of the *Mycosphaerella brassicicola* resistant *Brassica oleracea* plant according to claim 6 and comprising in its genome the resistance providing genomic fragment comprising SEQ ID No. 1, SEQ ID No. 3, SEQ ID No. 5, and SEQ ID No. 7.

* * * * *